United States Patent
Kishida et al.

(10) Patent No.: US 7,055,955 B2
(45) Date of Patent: Jun. 6, 2006

(54) EYE FUNDUS EXAMINATION APPARATUS

(75) Inventors: Nobuyoshi Kishida, Tochigi (JP); Shigeaki Ono, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 336 days.

(21) Appl. No.: 10/086,139

(22) Filed: Feb. 26, 2002

(65) Prior Publication Data

US 2002/0131017 A1 Sep. 19, 2002

(30) Foreign Application Priority Data

Feb. 27, 2001  (JP) .......................................... 2001-052832
Jun. 29, 2001  (JP) .......................................... 2001-197948

(51) Int. Cl.
*A61B 3/10* (2006.01)
*G09G 5/00* (2006.01)

(52) U.S. Cl. .................................... 351/205; 345/700
(58) Field of Classification Search ................. 351/200, 351/205, 206, 209–211, 213–216, 221; 600/476, 600/479, 504, 558; 396/18; 356/28; 345/700, 345/761, 764, 765, 766, 775–779, 781, 788
See application file for complete search history.

(56) References Cited

U.S. PATENT DOCUMENTS

| | | | | | |
|---|---|---|---|---|---|
| 4,436,388 A | * | 3/1984 | Takahashi et al. | ........... | 351/206 |
| 4,952,050 A | * | 8/1990 | Aizu et al. | ................... | 351/221 |
| 5,830,147 A | * | 11/1998 | Feke et al. | ................... | 600/479 |
| 5,844,658 A | * | 12/1998 | Kishida et al. | .............. | 351/206 |
| 6,411,839 B1 | * | 6/2002 | Okinishi | ...................... | 600/479 |
| 6,575,571 B1 | * | 6/2003 | Shibata | ........................ | 351/206 |

* cited by examiner

*Primary Examiner*—Max F. Hindenburg
*Assistant Examiner*—John R. Sanders
(74) *Attorney, Agent, or Firm*—Morgan & Finnegan, LLP

(57) ABSTRACT

In an eye fundus examination apparatus such as an eye fundus blood flowmeter, the display on a monitor is changed depending on the detection stage of the eye fundus examination apparatus. When measurement is started, an eye fundus image is zoomed to allow an easy check on the measurement state of the eye fundus. When the measurement is completed, the eye fundus image is restored to its initial size. This makes it possible to easily observe a measurement region during measurement and facilitate observation of measurement data after the measurement. In addition, when an eye fundus image is to be zoomed, a measurement region can be reliably observed by positioning the measurement position in the center of the monitor.

15 Claims, 16 Drawing Sheets

FIG. 13

| | x[n] | x[n+1] | x[n+2] | x[n+3] | x[n+4] | x[n+5] | x[n+6] | x[n+7] | x[n+8] | x[n+9] | x[n+10] | x[n+11] | x[n+12] | x[n+13] | x[n+14] | x[n+15] |
|---|---|---|---|---|---|---|---|---|---|---|---|---|---|---|---|---|
| y[n] | 0 | 0 | 0 | 0 | 0 | 0 | 0 | 0 | 0 | 0 | 0 | 0 | 0 | 0 | 0 | 0 |
| y[n+1] | 0 | 0 | 0 | 0 | 0 | 0 | 0 | 0 | 0 | 0 | 0 | 0 | 0 | 0 | 0 | 0 |
| y[n+2] | 0 | 0 | 0 | 0 | 0 | 0 | 0 | 0 | 0 | 0 | 0 | 0 | 0 | 0 | 0 | 0 |
| y[n+3] | 0 | 0 | 0 | 0 | 0 | 0 | 0 | 0 | 0 | 0 | 0 | 0 | 0 | 0 | 0 | 0 |
| y[n+4] | 0 | 0 | 0 | 0 | 0 | 0 | 1 | 1 | 0 | 0 | 0 | 0 | 0 | 0 | 0 | 0 |
| y[n+5] | 0 | 0 | 0 | 0 | 0 | 0 | 0 | 1 | 0 | 0 | 0 | 0 | 0 | 0 | 0 | 0 |
| y[n+6] | 0 | 0 | 0 | 0 | 0 | 0 | 0 | 1 | 1 | 0 | 0 | 0 | 0 | 0 | 0 | 0 |
| y[n+7] | 0 | 0 | 0 | 0 | 0 | 0 | 0 | 0 | 1 | 0 | 0 | 0 | 0 | 0 | 0 | 0 |
| y[n+8] | 0 | 0 | 0 | 0 | 0 | 0 | 0 | 0 | 1 | 1 | 0 | 0 | 0 | 0 | 0 | 0 |
| y[n+9] | 0 | 0 | 0 | 0 | 0 | 0 | 0 | 0 | 0 | 1 | 0 | 0 | 0 | 0 | 0 | 0 |
| y[n+10] | 0 | 0 | 0 | 0 | 0 | 0 | 0 | 0 | 0 | 1 | 1 | 0 | 0 | 0 | 0 | 0 |
| y[n+11] | 0 | 0 | 0 | 0 | 0 | 0 | 0 | 0 | 0 | 0 | 0 | 0 | 0 | 0 | 0 | 0 |
| y[n+12] | 0 | 0 | 0 | 0 | 0 | 0 | 0 | 0 | 0 | 0 | 0 | 0 | 0 | 0 | 0 | 0 |
| y[n+13] | 0 | 0 | 0 | 0 | 0 | 0 | 0 | 0 | 0 | 0 | 0 | 0 | 0 | 0 | 0 | 0 |
| y[n+14] | 0 | 0 | 0 | 0 | 0 | 0 | 0 | 0 | 0 | 0 | 0 | 0 | 0 | 0 | 0 | 0 |
| y[n+15] | 0 | 0 | 0 | 0 | 0 | 0 | 0 | 0 | 0 | 0 | 0 | 0 | 0 | 0 | 0 | 0 |

EYE FUNDUS EXAMINATION APPARATUS

BACKGROUND OF THE INVENTION

1. Field of the Invention

The present invention relates to an eye fundus examination apparatus for examining an eye fundus in an ophthalmic hospital, e.g., an eye blood flowmeter such as an eye fundus blood flowmeter for measuring a blood flow velocity and rate by illuminating an eye to be examined with a laser beam, receiving scattered reflected light, and analyzing it. In addition, the present invention relates to a method of displaying an eye fundus image and measurement data at the time of measurement of a blood flow velocity and rate.

2. Related Background Art

As a conventional eye blood flowmeter, a laser Doppler eye fundus blood flowmeter which tracks an eye fundus blood vessel of an eye to be examined and measures the absolute blood flow velocity in the tracked blood vessel is known. As such a laser Doppler eye fundus blood flowmeter, for example, the apparatus disclosed in Japanese Patent Application Laid-Open No. 07-31596 is known, which illuminates an eye fundus blood vessel with both a tracking laser beam and blood flow velocity measurement laser beam. This apparatus obtains the blood flow velocity in an eye fundus blood vessel and the vessel diameter of the measured blood vessel so as to measure the blood flow rate in the blood vessel.

The eye fundus blood flowmeter is an apparatus which illuminates an eye fundus blood vessel (to be examined) of an eye to be examined with a laser beam having a wavelength $\lambda$, receives the resultant scattered reflected light through a photodetector, detects an interference signal based on a Doppler-shifted component, which is scattered reflected light from a blood flow, and scattered reflected light from a blood vessel wall in a stationary state, and obtains a blood flow velocity by frequency-analyzing the signal. A blood flow velocity (maximum velocity Vmax) is obtained by the following principle.

$$\text{Vmax} = \{\lambda/(n \cdot \alpha)\} \cdot ||\Delta \text{fmax1}| - |\Delta \text{fmax2}||/\cos \beta$$

where $\Delta \text{fmax1}$ and $\Delta \text{fmax2}$ are the maximum frequency shifts calculated from the reception signals received by two light-receiving parts, $\lambda$ is the wavelength of a laser beam, n is the refractive index of a measurement region, $\alpha$ is the angle defined by two light-receiving axes in the eye, and $\beta$ is the angle defined by a plane formed by the two light-receiving axes in the eye and the velocity vector of a blood flow.

Such measurements in two directions cancel out the contribution of measurement light in the incidence direction. This makes it possible to measure a blood flow at an arbitrary region on the eye fundus. If the nodal line defined by the plane formed by two light-receiving axes and the eye fundus is matched with the velocity vector of a blood flow, then $\beta = 0°$. As a consequence, a true maximum blood flow velocity can be measured.

This laser Doppler eye fundus blood flowmeter, however, requires a measurement time of a few seconds, and hence the ophthalmic technician must perform measurement while observing the state of an eye to be examined. In using such an apparatus that requires to simultaneously observe the state of data under measurement and the state of an eye to be examined, an observed image obtained by a TV camera is displayed on an observation monitor, and the state of data under measurement is displayed on the monitor of a personal computer for blood flow velocity analysis. The ophthalmic technician can simultaneously observe the state of data under measurement and the state of the eye to be examined by simultaneously observing the two monitors.

In the above prior art, however, two monitors, i.e., a monitor for observation of an eye to be examined during measurement and a monitor for displaying the state of data under measurement, must be separately installed, posing problems in terms of space and ease of observation. In addition, recently, with a video capture board or the like, video signals can be displayed on the monitor screen of a personal computer, and an observed image of an eye to be examined can be displayed on the monitor screen of the personal computer for blood flow velocity analysis, together with measurement results and measurement conditions.

However, many pieces of information, e.g., an observed image of an eye to be examined, the state of data under measurement, and measurement results, must be displayed on the monitor. Assume that measurement results and measurement conditions are preferentially displayed. In this case, in performing alignment for a blood vessel to be measured, an observed image of an eye to be examined becomes small and difficult to see. In contrast to this, if an observed image of an eye to be examined is preferentially displayed, measurement results become difficult to see.

A conventional apparatus which picks up an eye fundus image by a TV camera and allows an operator to position the apparatus, select a measurement region, and perform measurement while observing a TV monitor has been disclosed in Japanese Patent Application Laid-Open Nos. 07-136141 and 07-155299 and the like. However, the display zooming ration of such apparatuses can not be changed. An ophthalmologic apparatus capable of changing the display zooming ratio is disclosed in Japanese Patent Application Laid-Open No. 08-126611. These ophthalmologic apparatuses have the following drawbacks.

(1) In extracting a measurement position on the eye fundus of an eye to be examined and performing positioning to match the optical axis of the eye to be examined with the optical axis of an objective lens, a low display zooming ratio, i.e., allowing the operator to see a wide range on the eye fundus, is preferable in searching for a measurement position candidate on the eye fundus. When positioning is to be performed, a wide range on the eye fundus which can be seen allows the operator to check mixture of external disturbance light and the like and perform accurate positioning.

(2) In checking whether a blood vessel to be measured is accurately illuminated with measurement light, a higher display zooming ratio allows the operator to obtain more detailed information and hence to make accurate setting.

In method (1), however, since the display zooming ratio is constant, it is impossible to satisfy both the requirements. Although two display means may be prepared, a large space is required, and an increase in cost is inevitable.

In method (2), since a central position is fixed when the zooming ratio is changed, if an actual measurement position is not near the central position when the zooming ratio is increased, the measurement position falls out of the display range.

Furthermore, although the zooming ratio can be optically changed, a complicated arrangement is required to simultaneously change the central position and the zooming ratio, resulting in a large, expensive apparatus.

SUMMARY OF THE INVENTION

It is an object of the present invention to provide an eye blood flowmeter which solve the above problems and allows an ophthalmic technician to easily see an observed image, a measurement result, and the like even if they are simultaneously displayed.

In order to achieve the above object, the present invention is characterized by including a blood flow measurement part which illuminates an eye blood vessel with a laser beam, receives reflected light, and obtains a blood flow velocity from the reflected light, a control part which controls a measurement state, image pickup means for picking up an image of an eye, a display which displays an observed image of the eye picked up by the image pickup means, and a control part which controls the display in accordance with the measurement state of the blood vessel measurement part.

The present invention is further characterized in that the control part has an illumination control part which controls illumination of a laser beam, and controls a display method for the display in accordance with an output from the illumination control part.

The present invention is further characterized in that the control part zooms and displays an image displayed on the display at the start of laser beam illumination.

The present invention is further characterized in that the control part cancels zooming of an image displayed on the display at the end of laser beam illumination.

It is another object of the present invention to provide an eye fundus examination apparatus which solves the above problems and can accurately display an examination region position on a central portion even if the display position and zooming ratio are changed.

In order to achieve the above object, the present invention is characterized by including an illumination optical system which illuminates the eye fundus of an eye to be examined with illumination light, a beam illumination optical system which illuminates the eye fundus with an illumination beam, a beam deflection means which is placed in the beam illumination optical system and deflects the illumination beam, image pickup means for picking up an eye fundus image and an illumination beam image and outputting an image signal by, display means for displaying the eye fundus image and illumination beam image on the basis of the image signal from the image pickup means, illumination beam position detection means for detecting the eye fundus position illuminated with the illumination beam, and display information changing means for changing at least one of the display position and zooming ratio of the eye fundus image and illumination beam image displayed on the display means.

The above and other objects, features, and advantages of the present invention will be apparent from the following detailed description in conjunction with the accompanying drawings and the appended claims.

BRIEF DESCRIPTION OF THE DRAWINGS

FIG. 13 is a view showing the distribution of a tracking target image extracted from the pixels of a G signal in a two-dimensional CCD camera;

DETAILED DESCRIPTION OF THE PREFERRED EMBODIMENTS

The present invention will be described in detail hereinafter based on the illustrated embodiments.

(First Embodiment)

Figure 1:
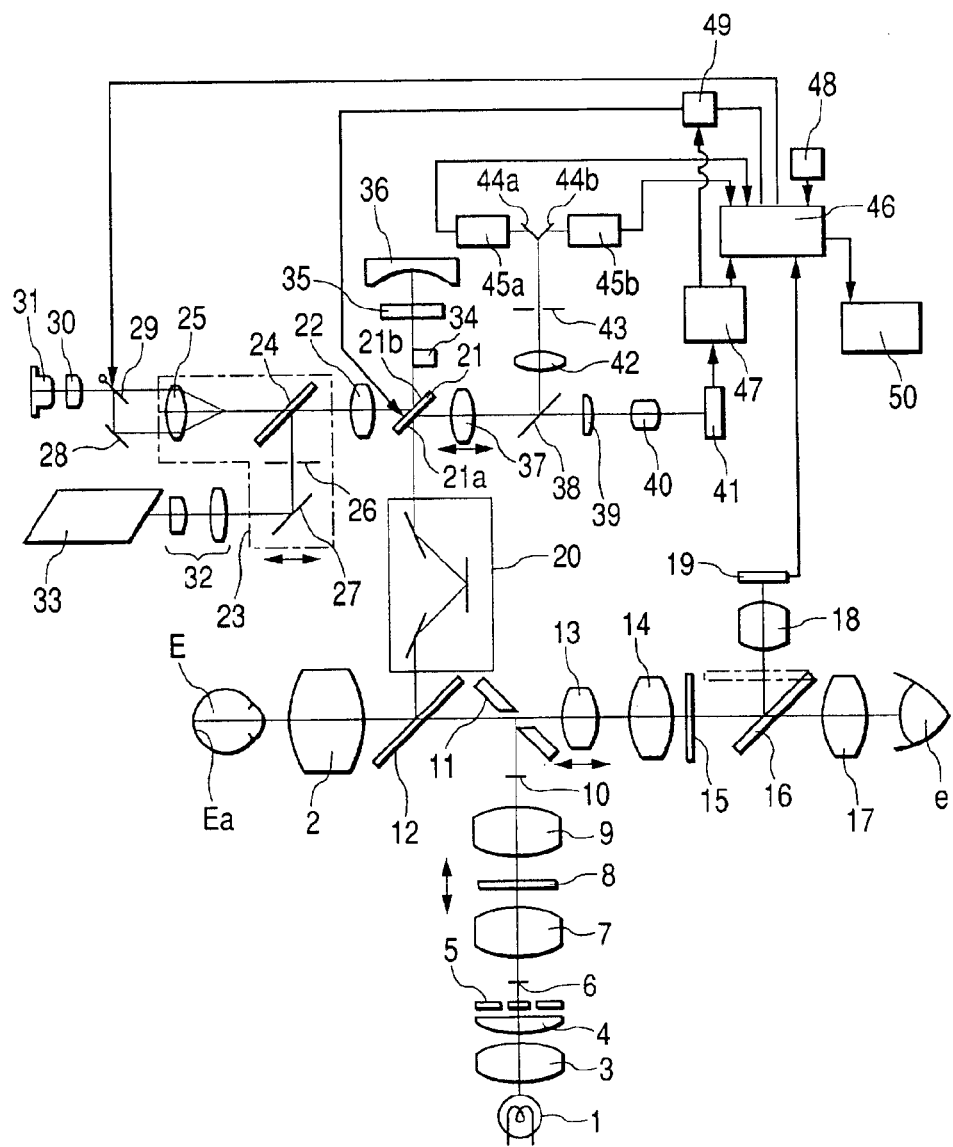
FIG. 1 is a view showing the arrangement of an eye blood flowmeter according to the first embodiment.

FIG. 1 shows the arrangement of a fundus blood flowmeter of the first embodiment. On an illumination optical path extending from an observation light source 1 comprising, e.g., a tungsten lamp for emitting white light to an objective lens 2 that opposes an eye E to be examined, a condenser lens 3, a field lens 4 with a bandpass filter that transmits only wavelength light in, e.g., the yellow wavelength range, a ring slit 5 which is set at a position nearly conjugate to the pupil of the eye E to be examined, a light-shielding member 6 which is set at a position nearly conjugate to a lens of the eye E to be examined, a relay lens 7, a transmission liquid crystal panel 8 which is a fixation target display element movable along the optical path, a relay lens 9, a light-shielding member 10 which is conjugate to a position near the cornea of the eye E to be examined, an apertured mirror 11, and a bandpass mirror 12 which transmits wavelength light in the yellow wavelength range and reflects most of other light beams, are sequentially arranged.

An eye observation optical system is built behind the apertured mirror 11, and a first focusing lens 13 which is movable along the optical path, a relay lens 14, a scale plate 15, an optical path switching mirror 16 which is free to be inserted into or removed from the optical path, and an eyepiece 17 are sequentially arranged along the optical path that leads to an eye E of an ophthalmic technician. On the optical path in the reflecting direction with the optical path switching mirror 16 being inserted in the optical path, a TV relay lens 18 and CCD camera 19 serving as an image pickup device are arranged.

On the optical path in the reflecting direction of the bandpass mirror 12, an image rotator 20 and a galvanometric mirror 21 having a rotation axis perpendicular to the drawing surface are disposed. Both lower and upper reflection surfaces 21a and 21b of the galvanometric mirror 21 are polished. A lens 22 and a focus unit 23 which is movable along the optical path are placed in the reflecting direction of the upper reflection surface 21b. Note that the front focal plane of the lens 22 is conjugate to the pupil of the eye E to be examined, and the galvanometric mirror 21 is located on this focal plane. In the focus unit 23, a dichroic mirror 24 and condenser lens 25 are sequentially disposed on the same optical path as the lens 22, and a mask 26 and mirror 27 are disposed on the optical path in the reflecting direction of the dichroic mirror 24. The focus unit 23 is integrally movable in a direction indicated by the arrow.

On the optical path in the incidence direction of the condenser lens 25, a stationary mirror 28 and an optical path switching mirror 29 which is retractable from the optical path are arranged in parallel. On the optical path in the incidence direction of the optical path switching mirror 29, a collimator lens 30 and a measurement laser diode 31 that emits coherent red light are arranged. On the optical path in the incidence direction of the mirror 27, a beam expander 32 which comprises a cylindrical lens and the like, and a tracking light source 33 that emits, e.g., high-luminance green light, which is different from the light emitted from another light source, are arranged.

Behind the galvanometric mirror 21, an optical path length compensation meniscus plate 34, a sunspot plate 35 having a light-shielding portion in the optical path, and a concave mirror 36 are arranged to form a relay optical system that guides a light beam transmitted through the lower reflection surface 21a of the galvanometric mirror 21 without being reflected to the upper reflection surface 21b of the galvanometric mirror 21.

On the optical path in the reflecting direction of the lower reflection surface 21a of the galvanometric mirror 21, a second focusing lens 37 that is movable along the optical path, a dichroic mirror 38, a field lens 39, an enlargement lens 40, and a linear CCD 41 with an image intensifier are sequentially arranged to form a blood vessel detection system.

On the optical path in the reflecting direction of the dichroic mirror 38, an imaging lens 42, a confocal stop 43, and a pair of mirrors 44a and 44b that are nearly conjugate to the pupil of the eye E to be examined are arranged. Photomultipliers 45a and 45b are respectively placed in the reflecting directions of the pair of mirrors 44a and 44b to form a measurement light-receiving optical system.

Note that all the optical paths are illustrated on the same plane for the sake of illustrative convenience. However, the reflecting optical paths of the mirrors 44a and 44b, the measurement optical path in the exit direction of the tracking light source 33, and the optical path extending from the laser diode 31 to the mask 26 are perpendicular to the drawing surface.

A system control unit 46 controls the entire apparatus. The outputs of the CCD camera 19, linear CCD 41 through a blood vessel position detection circuit 47, an input device 48 allowing the ophthalmic technician to operate the apparatus, and the photomultipliers 45a and 45b are connected to the system controller 46. The output of the system control unit 46 is connected to a mirror control circuit 49 for controlling the galvanometric mirror 21, the optical path switching mirror 29, and a display 50. In addition, the output of the linear CCD 41 is connected to the mirror control circuit 49 through the blood vessel position detection circuit 47.

Figure 2:
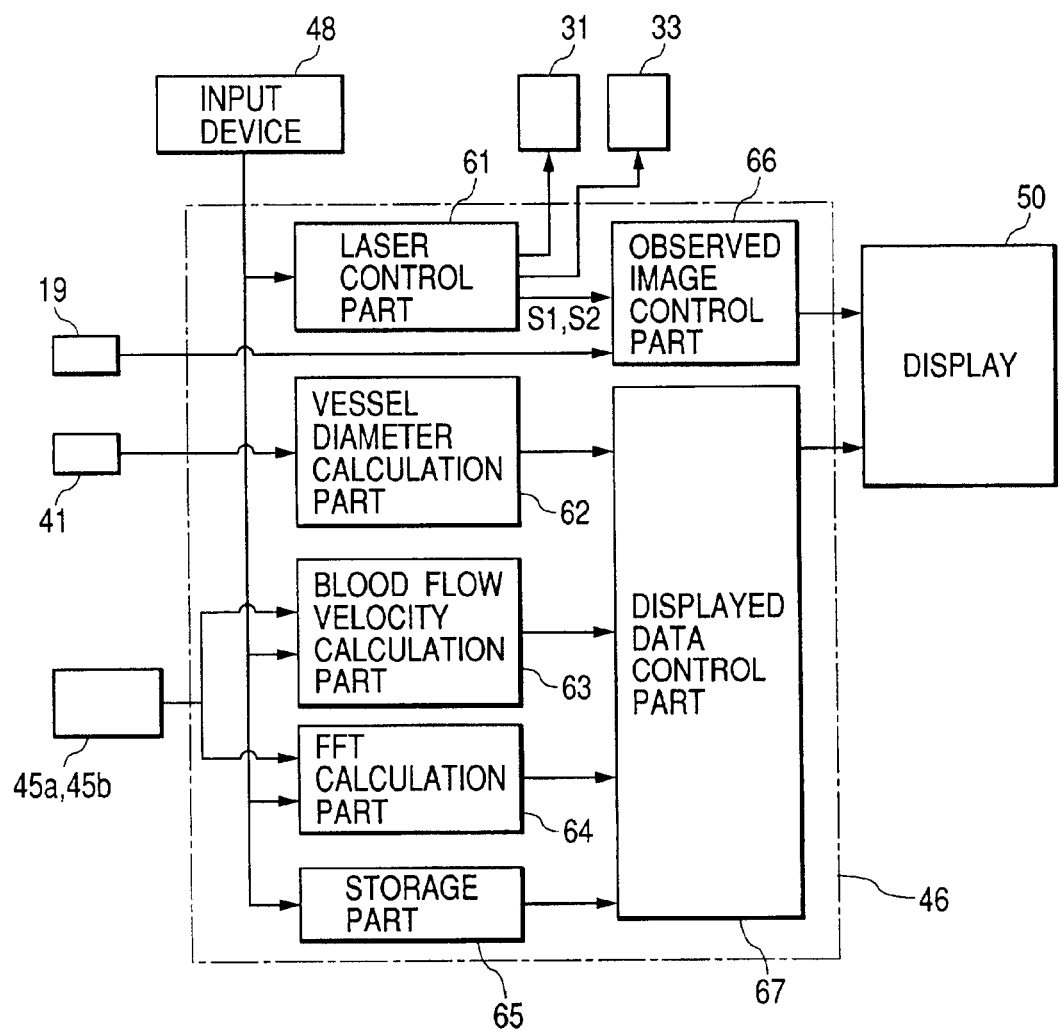
FIG. 2 is a block diagram showing the arrangement of a system controller.

FIG. 2 shows the arrangement of the system controller 46. The output of the input device 48 having a keyboard and measurement start switch is connected to the system controller 46. The system controller 46 includes a laser control part 61 for controlling illumination of tracking light from the tracking light source 33 and measurement light from the laser diode 31, a vessel diameter calculation part 62 for calculating a blood vessel diameter on the basis of a blood vessel image picked up by the linear CCD 41, a blood flow velocity calculation part 63 for calculating the blood flow velocity of the eye fundus Ea by frequency-analyzing light reception signals on the photomultipliers 45a and 45b, an FFT calculation part 64 for frequency-converting the light reception signals on the photomultipliers 45a and 45b, and a storage part 65 including a memory on which the patient information input through the input device 48 and measurement conditions such as a measurement time are recorded. Furthermore, the laser control part 61 is connected to an observed image control part 66 to which a signal from the CCD camera 19 is input. Signals from the vessel diameter calculation part 62, blood flow velocity calculation part 63, FFT calculation part 64, and storage part 65 are output to a displayed data control part 67. Signals from the observed image control part 66 and displayed data control part 67 are output to the display 50.

White light emitted from the observation light source 1 passes through the condenser lens 3, and only yellow wavelength light is transmitted through the field lens 4. The yellow wavelength light passes through the ring slit 5, light-shielding member 6, and relay lens 7, and illuminates the transmission liquid crystal panel 8 from behind. The light transmitted through the liquid crystal panel 8 passes through the relay lens 9 and light-shielding member 10, and is reflected by the apertured mirror 11. Only the wavelength light in the yellow wavelength range is then transmitted through the bandpass mirror 12, passes through the objective lens 2, temporarily forms an eye illumination light optical image I on the pupil of the eye E to be examined, and then nearly uniformly illuminates the eye fundus Ea. At this time, a fixation target is displayed on the transmission liquid crystal panel 8 and is projected on the eye fundus Ea of the eye E to be examined with the illumination light so as to be presented as a target image on the eye E to be examined. Note that the ring slit 5 and the light-shielding members 6 and 10 are used to split light into eye illumination light and eye observation light at a position in front of the eye E to be examined, and their shapes are not particularly limited as long as they can form a required light-shielding region.

The reflected light from the eye fundus Ea returns along the same optical path to be extracted as eye observation light from the pupil, and passes through the central aperture portion of the apertured mirror 11, first focusing lens 13, and relay lens 14. The light is formed into an eye fundus image Ea' on the scale plate 15, and reaches the optical path switching mirror 16. If the optical path switching mirror 16 is retracted from the optical path, the eye fundus image Ea' can be observed with the eye E of an ophthalmic technician through the eyepiece 17. If the optical path switching mirror 16 is inserted in the optical path, the eye fundus image Ea' formed on the scale plate 15 is formed again on the CCD camera 19 through the TV relay lens 18 and is displayed on the display 50 through the system controller 46.

Measurement light emitted from the laser diode 31 is collimated by the collimator lens 30. When the optical path switching mirror 29 is inserted in the optical path, this light is reflected by the optical path switching mirror 29 and stationary mirror 28 and passes through a lower portion of the condenser lens 25. When the optical path switching mirror 29 is retracted from the optical path, the light directly passes through an upper portion of the condenser lens 25. The light emerging from the condenser lens 25 is then transmitted through the dichroic mirror 24.

The beam size of tracking light emitted from the tracking light source 33 is expanded at different vertical and horizontal zooming ratios by the beam expander 32, and the tracking light is then reflected by the mirror 27. After that, the tracking light is shaped into a desired pattern by the shaping mask 26, and is reflected by the dichroic mirror 24 to be superposed on the measurement light described above.

The measurement light then forms a spot image at a position conjugate to the center of the aperture of the mask 26 by the focusing lens 25. In addition, the measurement light and tracking light pass through the lens 22 and are reflected by the upper reflection surface 21b of the galvanometric mirror 21. The reflected light beams then pass through the sunspot plate 35, are reflected by the convex mirror 36, pass through the sunspot plate 35 and meniscus plate 34 again, and are transmitted through the galvanometric mirror 21.

At this time, the galvanometric mirror 21 is located at a position conjugate to the eye E to be examined. In addition, the convex mirror 36, sunspot plate 35, and meniscus plate 34 are concentrically arranged on the optical path to provide the function of a relay optical system that forms once (1×) images of the upper and lower reflection mirrors 21b and 21a of the galvanometric mirror 21 in cooperation with each other. The measurement light and tracking light transmitted through the galvanometric mirror 21 are deflected toward the objective lens 2 by the bandpass mirror 12 through the image rotator 20, and illuminate the eye fundus Ea of the eye E to be examined through the objective lens 2.

Note that the meniscus plate 34 is used to correct deviations of the positions of the upper and lower reflection surfaces 21b and 21a of the galvanometric mirror 21 in the up-and-down direction on the drawing surface due to their mirror thickness, and has an effect in only the optical path extending toward the image rotator 20.

In this manner, the measurement light and tracking light are reflected by the upper reflection surface 21b of the galvanometric mirror 21 and incident on the galvanometric mirror 21 while they are offset from the optical axis of the objective lens 2 so as to be returned again. Scattered reflected light at the eye fundus Ea is focused again by the objective lens 2, reflected by the bandpass mirror 12, and passes through the image rotator 20. This light is then reflected by the lower reflection surface 21a of the galvanometric mirror 21, passes through the focusing lens 37, and is split into measurement light and tracking light by the dichroic mirror 38.

The tracking light passes through the dichroic mirror 38 and forms a blood vessel image, enlarged as compared with the eye fundus image Ea' obtained by the eye observation optical system, on the linear CCD 41 through the field lens 39 and enlargement lens 40. The blood vessel position detection circuit 47 creates data representing the moving amount of the blood vessel image on the basis of the blood vessel image picked up by the linear CCD 41, and outputs it to the mirror control circuit 49. The mirror control circuit 49 drives the galvanometric mirror 21 to compensate for this moving amount. The system controller 46 calculates a blood vessel diameter on the basis of the blood vessel image picked up by the linear CCD 41.

The measurement light is reflected by the dichroic mirror 38. The reflected light passes through the aperture portion of the confocal stop 43 and is reflected by the pair of mirrors 44a and 44b to strike the photomultipliers 45a and 45b. The light reception signals obtained by the photomultipliers 45a and 45b are output to the system controller 46. The system controller 46 then obtains the blood flow velocity of the eye fundus Ea by frequency-analyzing the light reception signals.

In this manner, the system controller 46 calculates a blood vessel diameter from the blood vessel image picked up by the linear CCD 41, and, as the result, a blood flow velocity can be calculated from light reception signals on the photomultipliers 45a and 45b. The calculated blood vessel diameter and blood flow velocity are output to the display 50.

Figure 3:
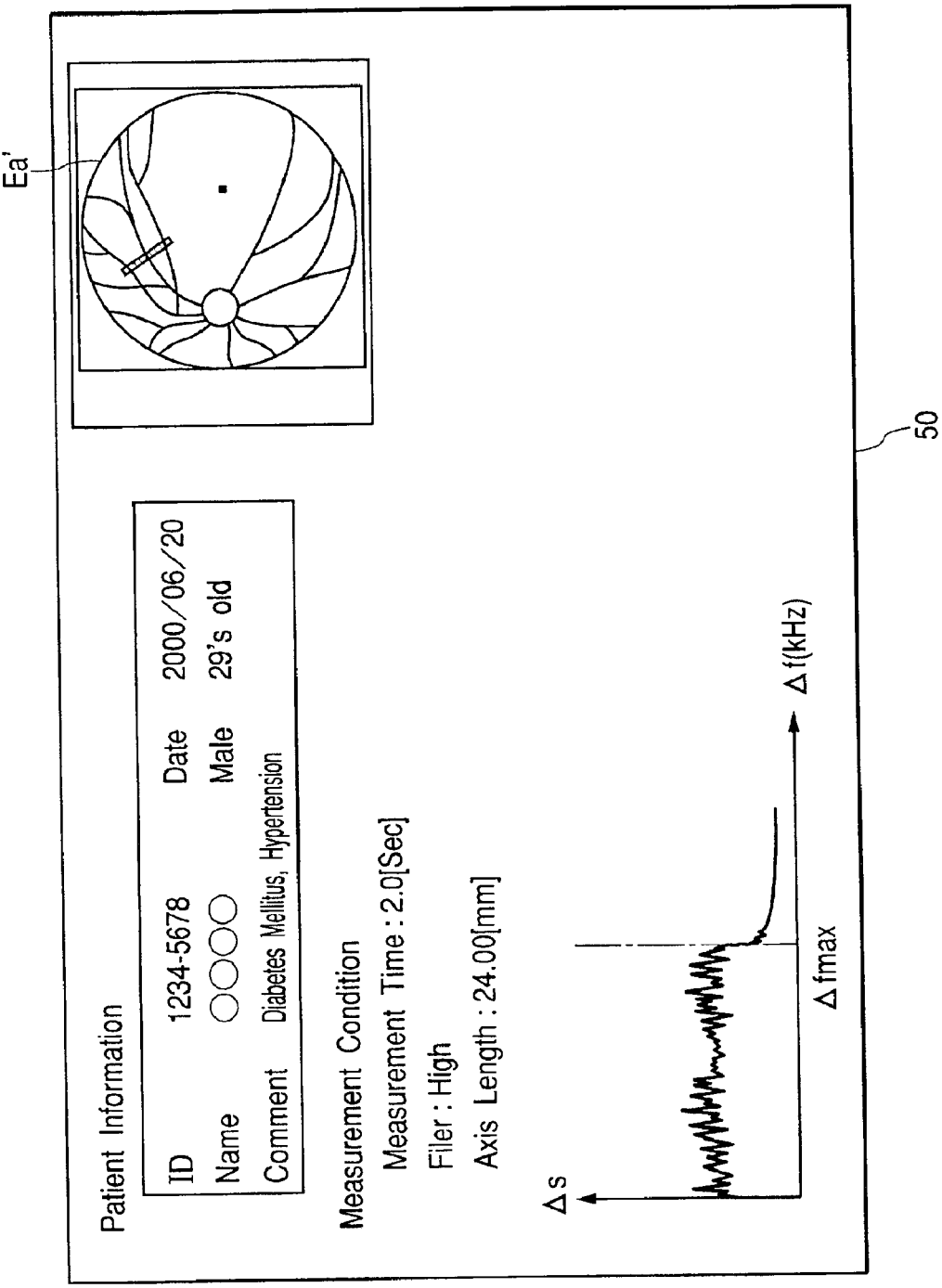
FIG. 3 is a view showing a display window on a display.

FIG. 3 is a display window of the display 50. The display 50 can display all pieces of information, e.g., calculation results on a blood vessel diameter, a blood flow velocity, and the like, information of an eye to be examined, and measurement conditions, together with the eye fundus image Ea' of the eye E to be examined which is picked by the CCD camera 19.

The ophthalmic technician performs alignment of the apparatus while observing the eye fundus image Ea' through the eyepiece 17 or display 50. In this case, an appropriate observation scheme is preferably used in accordance with the purpose. Observation with the eyepiece 17 is suitable for a diagnosis to be made by reading small changes in the eye fundus Ea because the eyepiece 17 is generally higher in resolution and sensitivity than the display 50 which displays all pieces of information, e.g., calculation results on a blood vessel diameter and blood flow velocity and measurement conditions, together with an eye fundus image of the eye E to be examined.

Observation with the display 50 is clinically very effective for the following reasons. The display 50 can reduce the fatigue of the ophthalmic technician because it does not limit the visual field. In addition, changes in a measurement region on the eye fundus image Ea' can be sequentially and electronically recorded by connecting the output of the CCD camera 19 to an external video tape recorder, video printer, or the like.

A procedure for the execution of a series of measuring operations using this apparatus will be described next. First of all, to input patient information such as a name, registration date, sex, age and comment, the ophthalmic technician inputs a patient ID by using the keyboard of the input device 48. In this case, if the patient ID has already been registered in the storage part 65, the name, registration date, sex, age and comment are displayed on the upper left portion of the window on the display 50, together with the measurement data immediately before this input operation, when the patient ID is input. If the patient ID is input for the first time, the ophthalmic technician inputs a name, registration date, sex, age and comment by using the keyboard of the input device 48, and no measurement data is displayed on the window on the display 50.

When patient information is completely input, the eye fundus Ea of the eye E to be examined is aligned. In this case, an observed image of the eye fundus image Ea' displayed on the upper right part of the window in FIG. 3 is large enough to perform alignment. A blood vessel to be measured is then determined, and the laser illumination switch of the input device 48 is pressed. The displayed data control part 67 receives an FFT signal from the FFT calculation part 64 which frequency-converts light reception signals on the photomultipliers 45a and 45b. Upon reception of this FFT signal, the displayed data control part 67 switches to the FFT display mode to display FFT information on the lower left part of the window on the display 50.

Figure 4:
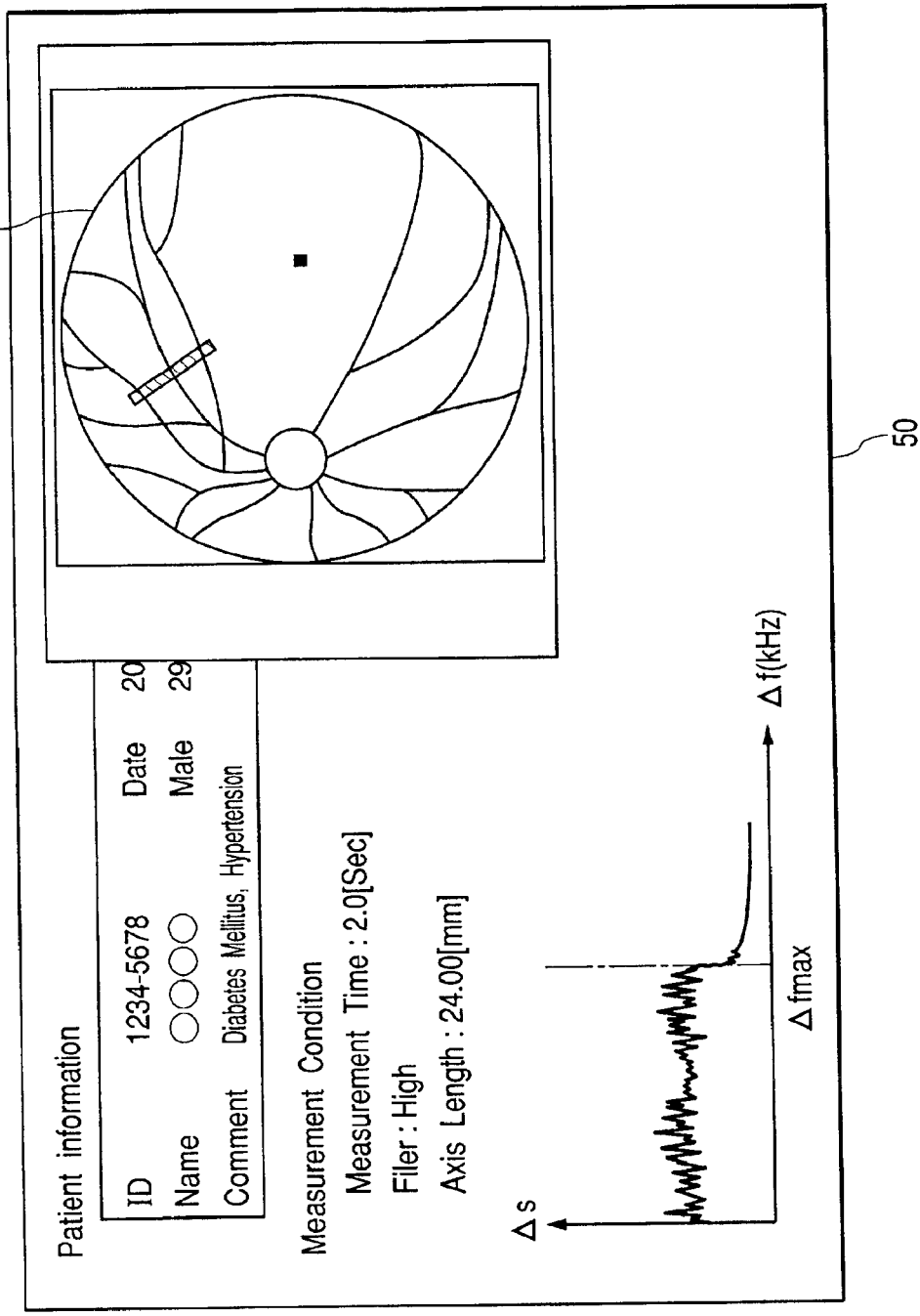
FIG. 4 is a view showing a display window on the display.

Upon reception of an input signal from the laser illumination switch, the laser control part 61 causes the tracking light source 33 and laser diode 31 to emit laser beams. At the same time, the laser control part 61 outputs an illumination start signal S1 to the observed image control part 66. Upon reception of the signal S1, the observed image control part 66 zooms and displays the eye fundus image Ea' from the CCD camera 19 on the display 50, as shown in FIG. 4. Obviously, at this time, zooming and displaying the observed image allows the ophthalmic technician to easily grasp the positional relationship between a blood vessel to be tracked and a tracking beam and to easily check whether measurement is reliably performed.

In this embodiment, since the measurement time is set to, e.g., two seconds, the vessel diameter calculation part 62 calculates a blood vessel diameter on the basis of the blood vessel image picked up by the linear CCD 41 and the blood flow velocity calculation part 63 calculates a blood flow velocity from light reception signals on the photomultipliers 45a and 45b for two seconds after the measurement start switch of the input device 48 is pressed.

As described above, according to this embodiment, an FFT display indicating a measurement state and a zoomed and displayed observed image can be simultaneously observed on the display 50 in the time interval between the instant at which laser illumination is started and the instant at which measurement is completed.

Figure 5:
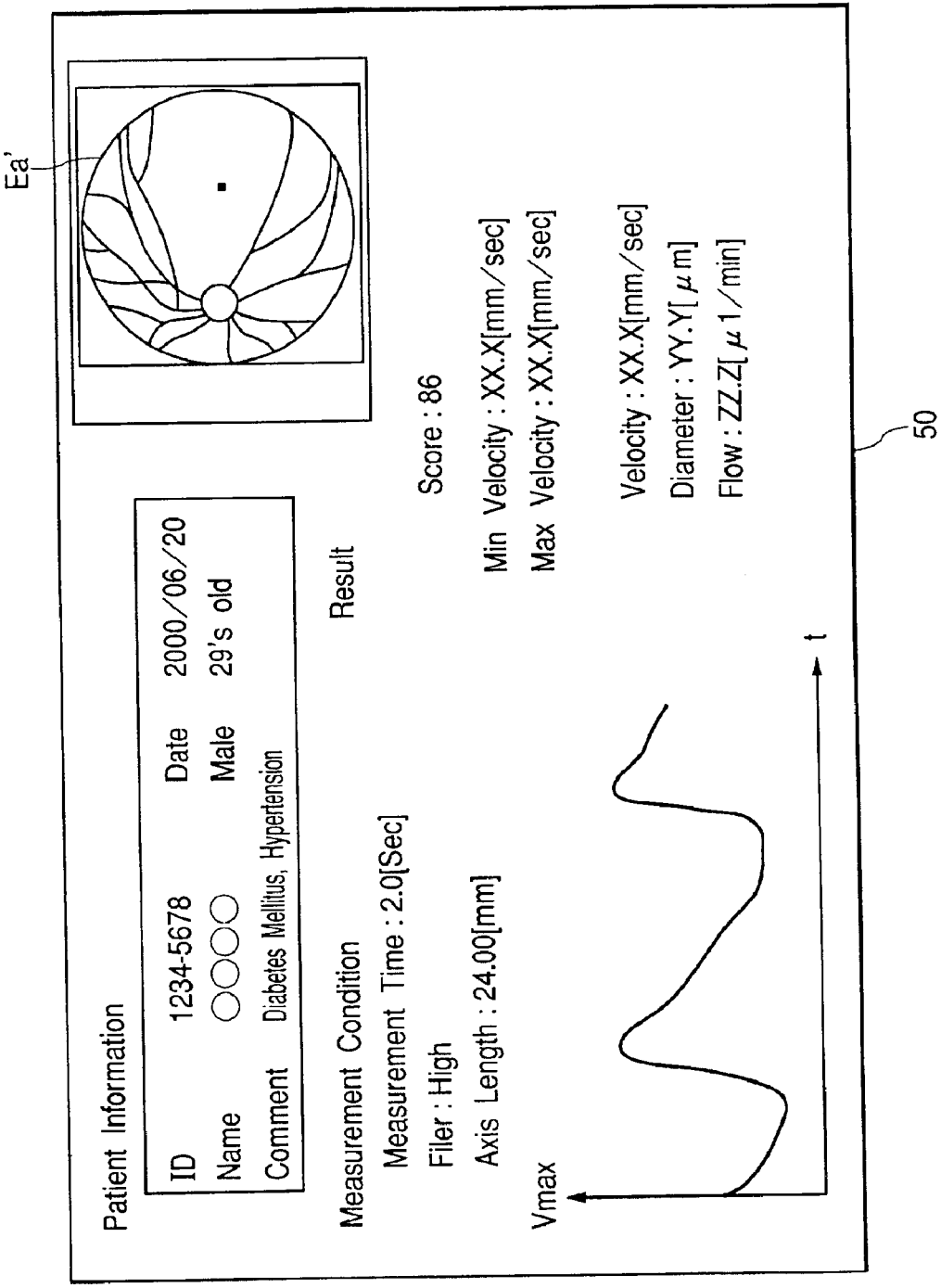
FIG. 5 is a view showing a display window on the display.

When two seconds measurement is completed upon reception of an input from the measurement start switch of the input device 48, the laser control part 61 stops laser illumination from the tracking light source 33 and laser diode 31, and outputs a laser illumination stop signal S2 to the observed image control part 66. Upon reception of the laser illumination stop signal S2, the observed image control part 66 cancels zooming and displaying of an observed image from the CCD camera 19, and displays the eye fundus image Ea' in the normal size on the display 50. The displayed data control part 67 also switches to the FFT display mode to the measurement result display mode. As a consequence, the display 50 performs the display operation shown in FIG. 5. In addition, the displayed data control part 67 receives blood vessel diameter data and blood flow velocity data from the vessel diameter calculation part 62 and blood flow velocity calculation part 63, graphs changes in blood flow velocity or calculates an average blood flow velocity or calculates, and a blood flow rate based on the blood vessel diameter and blood flow velocity, and displays them on the lower part of the window.

As described above, in this embodiment, when measurement is completed, FFT data indicating a measurement state is stopped to be displayed, and the eye fundus image Ea' is displayed on the display 50 while zooming and displaying operation is canceled, thus allowing the ophthalmic technician to check a graph indicating changes in blood flow velocity, an average blood flow velocity, and a blood flow rate.

In this embodiment, an observed image is zoomed and displayed by illumination of a laser beam. In addition, when laser illumination is stopped, zooming and displaying of an observed image is canceled. This makes it possible to easily grasp the positional relationship between a blood vessel to be tracked and a tracking beam during illumination of a laser beam. The ophthalmic technician can therefore check whether measurement is reliably performed, and checks the state of measurement data on the FFT monitor. When measurement is completed, the ophthalmic technician can check both a measurement result and an observed image by canceling zooming and displaying of the observed image.

In the first embodiment, when the optical path switching mirror 16 is retracted from the optical path, the CCD camera 19 picks up no observed image. The eye fundus image Ea' shown in FIGS. 3 and 5 or the like cannot therefore be observed. In this case, since the eye fundus image Ea' need not be zoomed and displayed, a signal indicating whether the optical path switching mirror 16 is retracted from the optical path may be input to the observed image control part 66. When the optical path switching mirror 16 is retracted from the optical path, the eye fundus image Ea' may not be zoomed.

(Second Embodiment)

Figure 6:
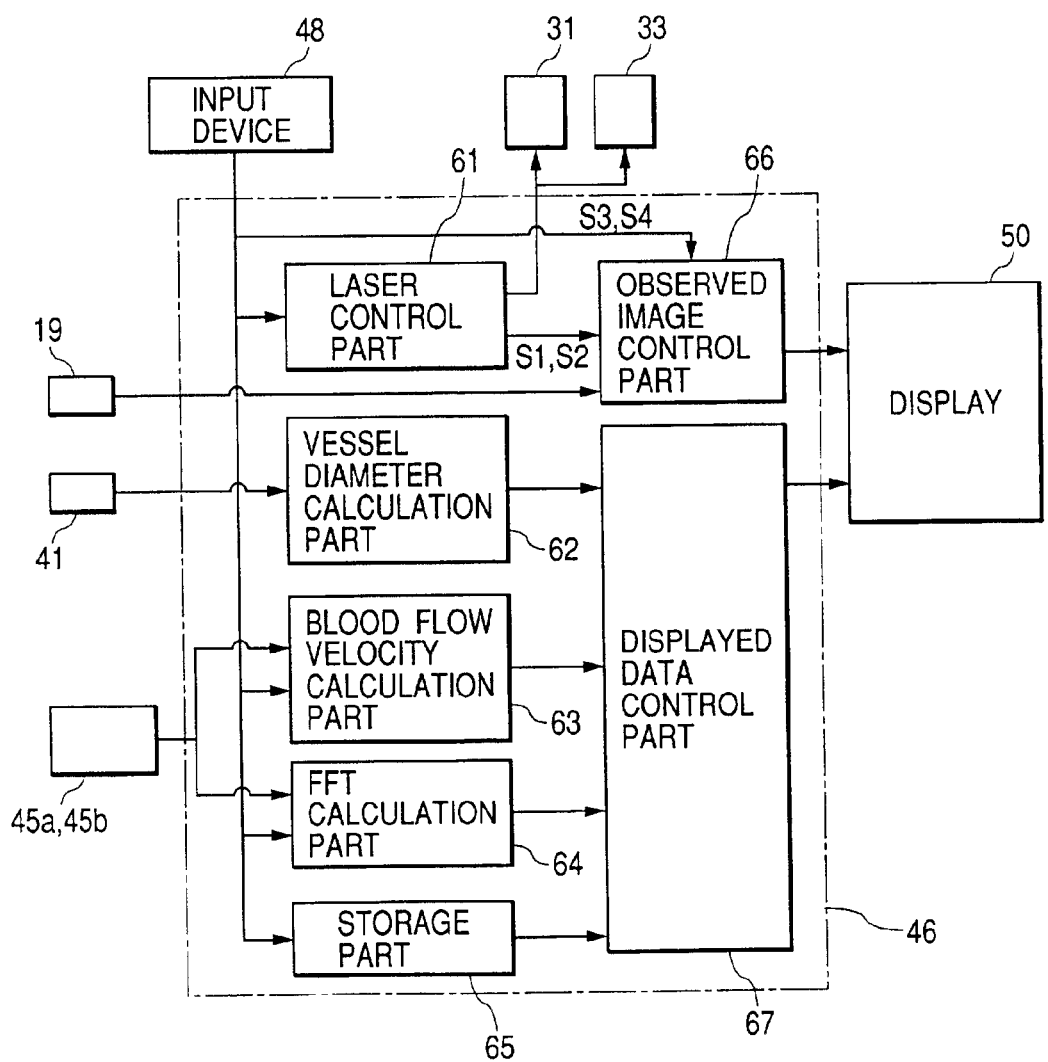
FIG. 6 is a block diagram showing the arrangement of a system controller.

The apparatus described above will suffice to observe a measurement result and an observed image in one window in a normal use. In the second embodiment, a zoom control switch for an observed image is mounted on an input device 48 to allow the ophthalmic technician to arbitrarily enlarge and display an observed image. With this operation, the ophthalmic technician can observe the state of an eye E to be examined in detail before measurement. In this case, the arrangement shown in FIG. 6 is used, which differs from the arrangement of the first embodiment in that the output of the input device 48 is connected to an observed image control part 66.

Figure 7:
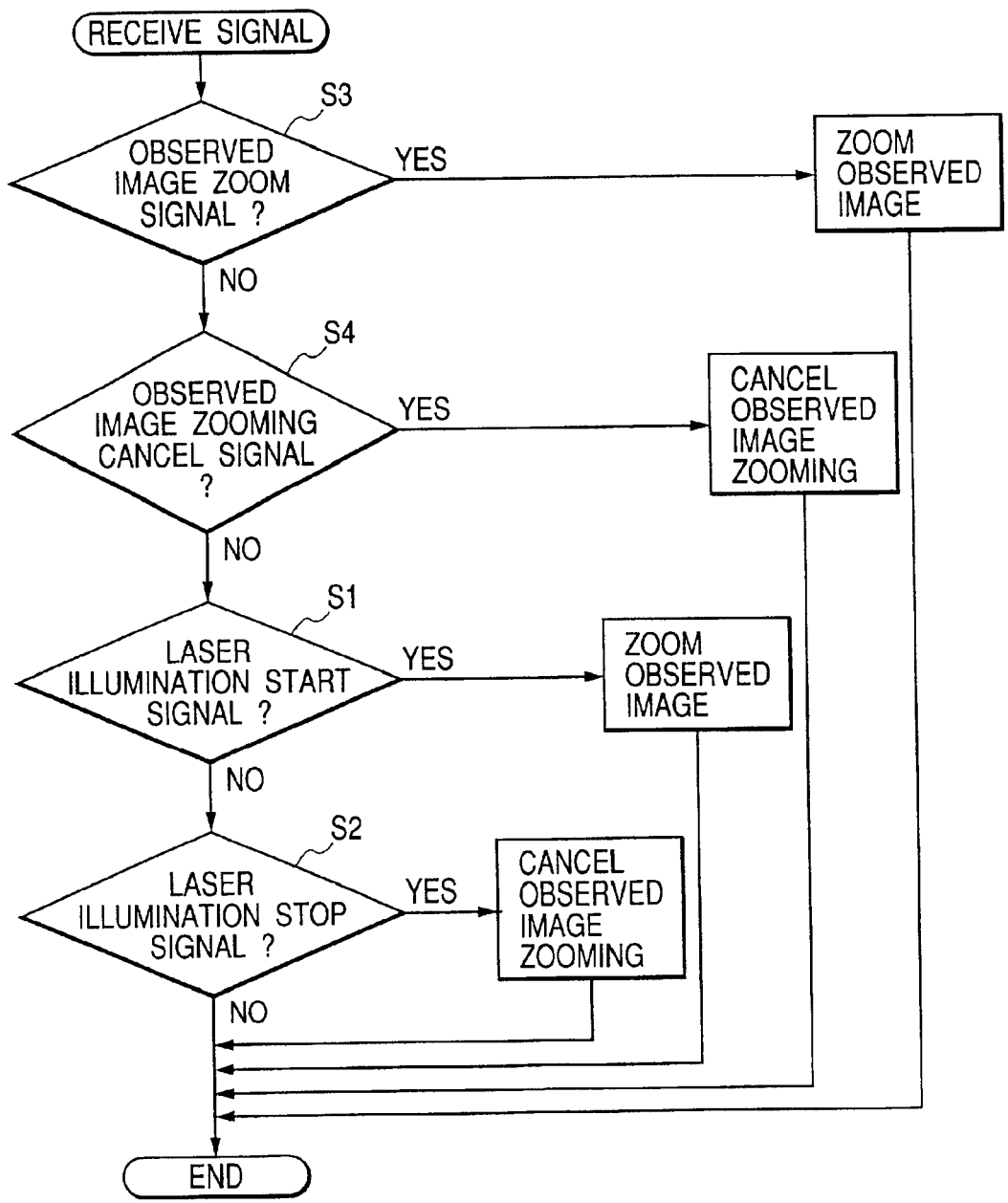
FIG. 7 is a flow chart showing internal processing.

FIG. 7 is a flow chart showing internal processing performed by the observed image control part 66 in the second embodiment. The observed image control part 66 checks the presence or absence of an input signal. Upon reception of an observed image zoom signal S3 from the zoom control switch of the input device 48, the observed image control part 66 zooms and displays an eye fundus image Ea' from a CCD camera 19 on a display 50. Upon reception of an observed image zooming cancel signal S4 from the zoom control switch of the input device 48, the observed image control part 66 cancels zooming and displaying of an observed image from the CCD camera 19 on the display 50. In this case, the observed image control part 66 performs operation based on the observed image zoom signal from the zoom control switch of the input device 48 preferentially with respect to an illumination start signal S1. For this reason, upon reception of the observed image zoom signal S3 before laser illumination, the observed image control part 66 zooms and displays an observed image on the display 50. Upon reception of the observed image zooming cancel signal S4 during laser illumination, the observed image control part 66 cancels zooming and displaying on the display 50.

Figure 8:
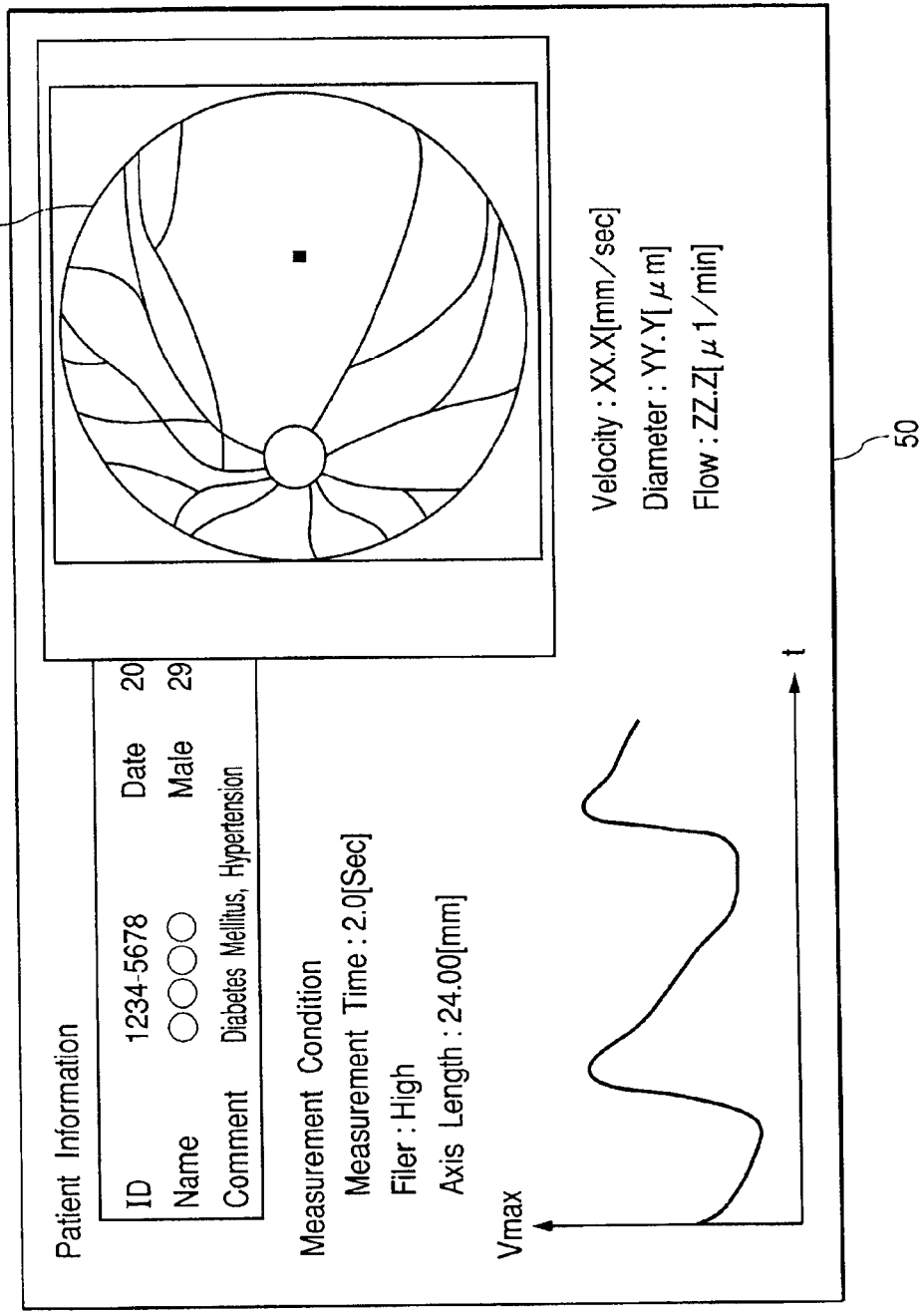
FIG. 8 is a view showing a display window on a display.

If, therefore, the ophthalmic technician wants to observe an observed image upon zooming and displaying it preferentially with respect to a measurement result during display of the measurement result, as shown in FIG. 3, he or she can zoom and display the eye fundus image Ea' by using the zoom control switch of the input device 48 as shown in FIG. 8. If the ophthalmic technician wants to preferentially observe measurement conditions upon reducing the eye fundus image Ea' during zooming and displaying the eye fundus image Ea', he or she can cancel zooming and displaying of the eye fundus image Ea' by using the zoom control switch of the input device 48.

As described above, according to the second embodiment, by mounting the zoom control switch for an observed image on the input device 48, the ophthalmic technician can preferentially observe a measurement result, measurement condition, or observed image regardless of the state of laser illumination. This makes it possible to provide an apparatus that is easy for the ophthalmic technician to use.

In the second embodiment, high priority is given to the zoom control switch for an observed image on the input device 48. However, there is hardly any need to control a window during measurement, and hence control by the zoom control switch may be inhibited to prevent the ophthalmic technician from erroneously operating the zoom control switch.

As described above, the eye blood flowmeter of the present invention is designed to change the observed image display state depending on the measurement state. This facilitates positioning operation for a blood vessel to be tracked. That is, this embodiment provides excellent effects in operation. In addition, since the positioning time can be shortened, the laser illumination time during positioning operation can be shortened. This makes it possible to reduce damage to the eye to be examined.

In addition, since the state of the display changes depending on the state of laser illumination, an observed image suitable for each measurement state can be displayed.

Furthermore, since the eye blood flowmeter of the present invention is designed to zoom an image on the display when laser illumination is started, a tracking state can be observed in detail.

Moreover, with the use of the eye blood flowmeter of the present invention, when the ophthalmic technician wants to stop laser illumination and check measurement results and measurement conditions, zooming of the observed image is canceled to allow he or she to check the measurement results and measurement conditions.

(Third Embodiment)

The third embodiment will be described with reference to FIGS. 9 to 17.

Figure 9:
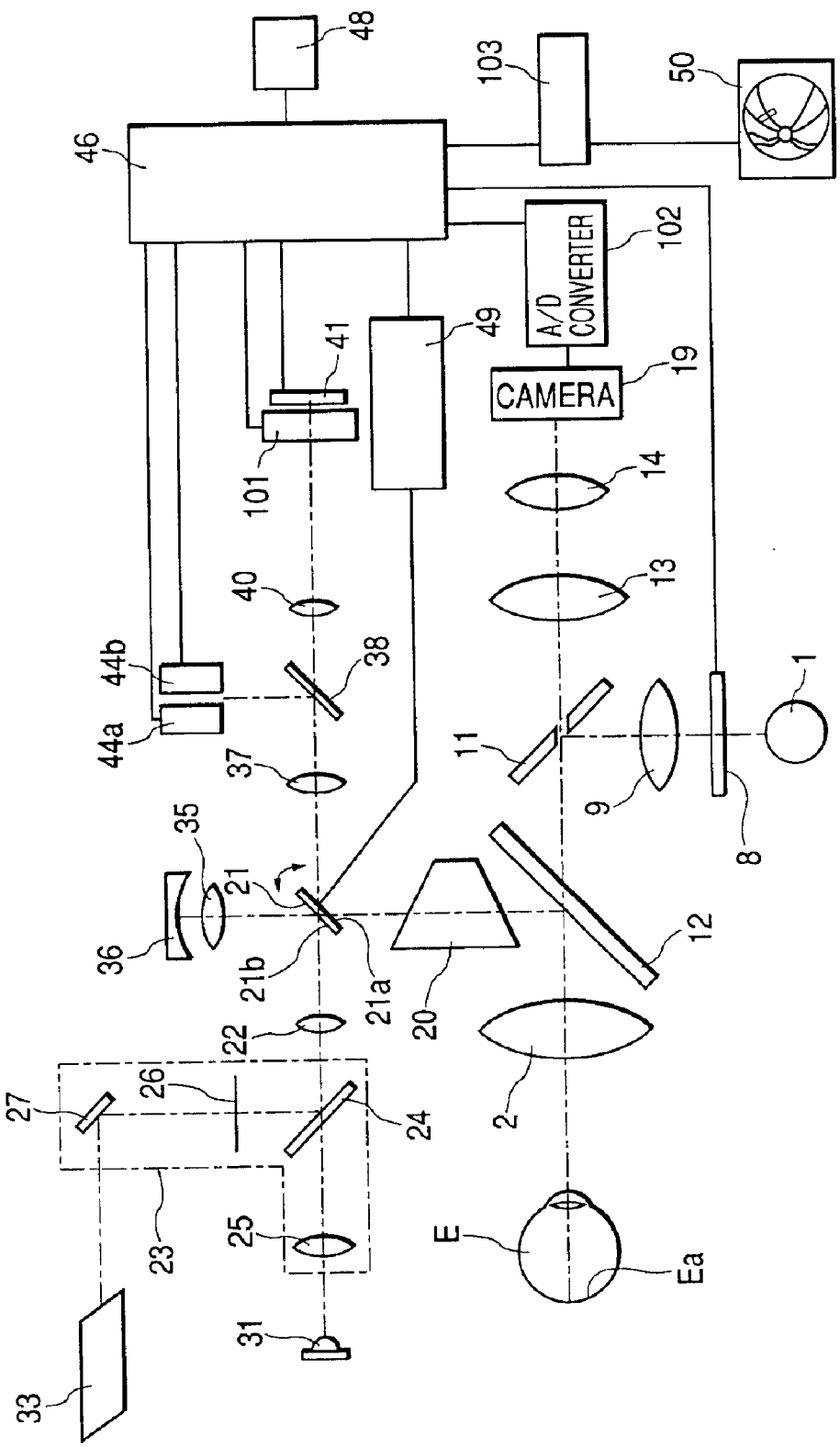
FIG. 9 is a view showing the arrangement of the third embodiment.

FIG. 9 shows the arrangement of the third embodiment. The same reference numerals as in FIG. 9 denote the same part in FIG. 1, and a description thereof will be omitted. An image intensifier 101 amplifies an input to a linear CCD 41.

An A/D converter 102 A/D-converts an output signal from a CCD camera 19. The digitally converted signal is read and processed by a system controller 46.

A D/A converter 103 converts an output from the system controller 46 into an analog signal and outputs it to a display 50 to display it.

Figure 10:
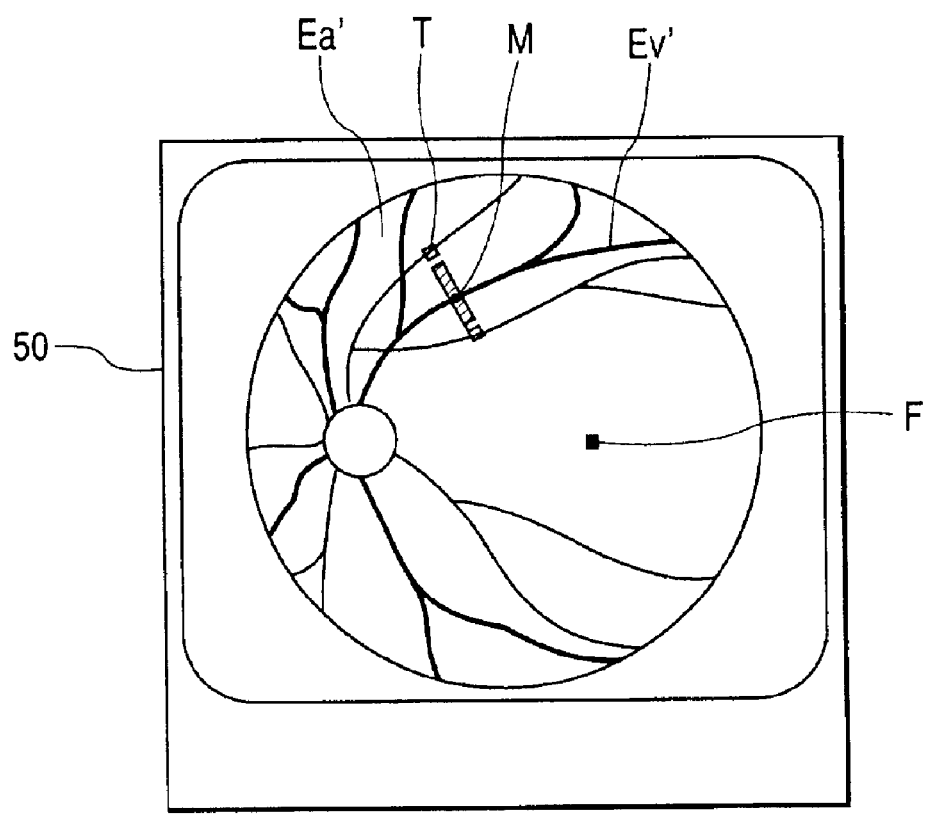
FIG. 10 is a view for explaining an observed eye fundus image after focusing operation which is not zoomed.

FIG. 10 shows an eye fundus image displayed on the display 50. The displayed window includes a fixation target F presented on the eye fundus by a transmission liquid crystal panel 8, a tracking target image T presented on the eye fundus by a tracking light source 33, a measurement light M presented on the eye fundus by a laser diode 31, and an eye fundus blood vessel image EV'. The ophthalmic technician can observe the fixation target F, tracking target image T, and measurement light M on the display 50, together with an observed eye fundus image Ea'.

The ophthalmic technician operates an operation console (not shown) to perform positioning to match the optical axis of an eye E to be examined with the optical axis of an objective lens 2. The ophthalmic technician then operates a focus knob to bring the eye fundus Ea of the eye E to be examined into focus while observing the eye fundus image Ea' on the display 50. As a consequence, as described above, the fixation target F of the transmission liquid crystal panel 8 optically becomes conjugate to the eye fundus Ea and is presented on the eye E to be examined.

The ophthalmic technician then selects a blood vessel to be measured. In this case, since the ophthalmic technician selects a blood vessel to be measured and a measurement region from a plurality of blood vessels, it is preferable that the eye fundus Ea can be observed in as wide a range as possible. This allows the ophthalmic technician to check the influence of external disturbance light and the like and perform accurate positioning. For these reasons, the ophthalmic technician inputs a request to zoom the eye fundus image Ea' displayed on the display 50 by using the input device 48, as needed.

Figure 11:
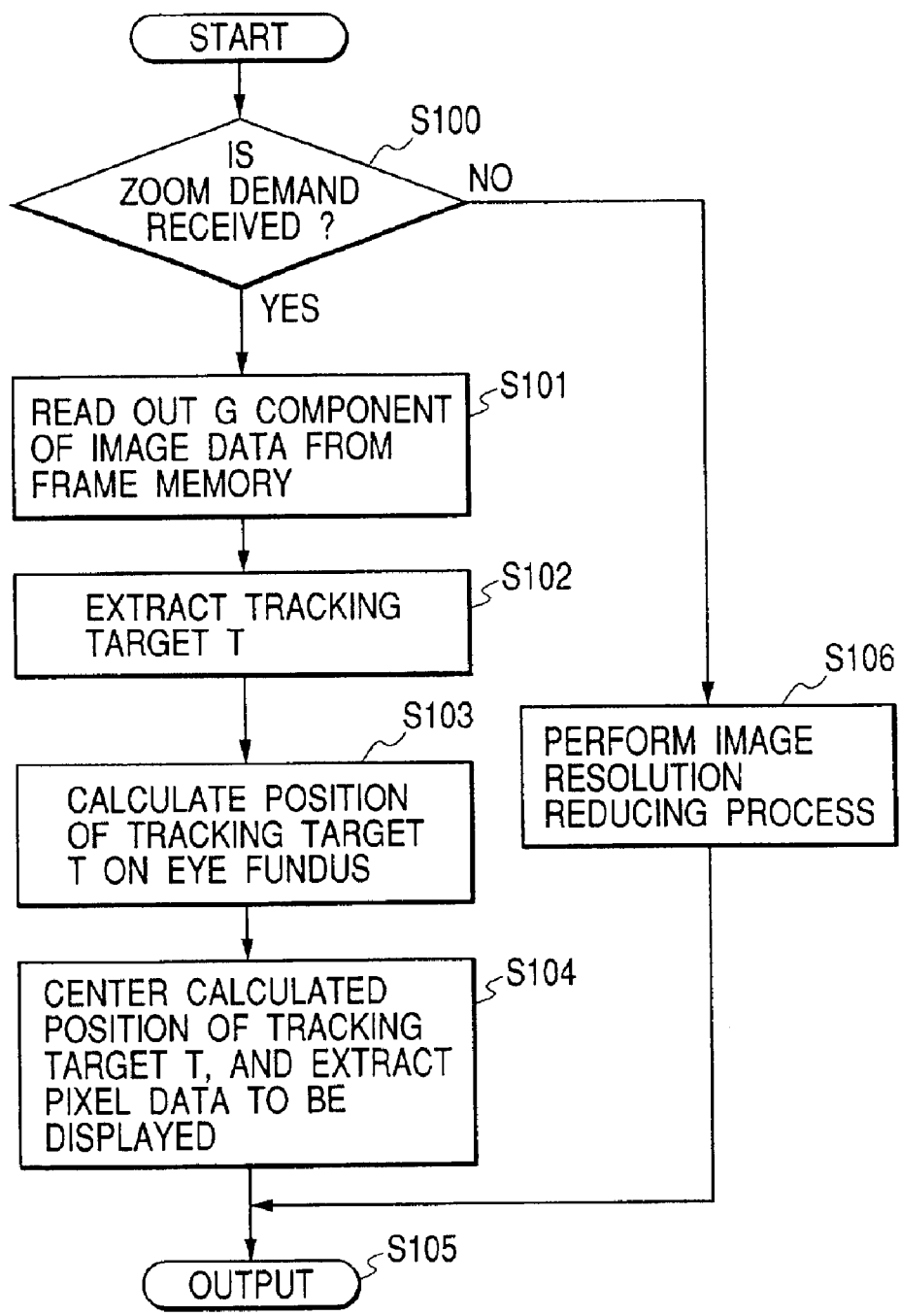
FIG. 11 is a flow chart in the third embodiment.

FIG. 11 is a flow chart showing the processing performed by the system controller 46. If the system controller 46 determines in step S100 that no zoom demand is input to an input device 48, the system controller 46 reads out image data from a frame memory and performs processing to decrease the resolution in step S106. In this embodiment, the number of pixels that can be picked up by the two-dimensional CCD camera 19 is larger than the resolution of the display 50. The processing in step S106 is performed to display the eye fundus image picked up by the two-dimensional CCD camera 19 on the display 50 throughout the entire range.

In step S105, this data is output to the D/A converter 103 to be converted into an analog video signal, and the observed eye fundus image Ea' illuminated with the tracking target image T and measurement light M is displayed on the display 50. The ophthalmic technician can observe the eye fundus image Ea' like the one shown in FIG. 10. At this time, the central position of the display 50 almost coincides with the optical axis of the objective lens 2.

Upon selecting a measurement region, the ophthalmic technician operates the input device 48 to move the fixation target F and guide the eye E to be examined such that the measurement region comes close to almost the center of the observation field. The ophthalmic technician then operates the input device 48 to illuminate the eye fundus Ea with tracking light, and also operates a rotator operation knob to set the tracking target image T to be vertical to a blood vessel Ev to be measured. In addition, the ophthalmic technician controls the angle of a galvanometric mirror 21 to illuminate the blood vessel Ev to be measured with the measurement light M.

At this time, the ophthalmic technician must check whether the tracking target image T is vertical to the blood vessel Ev to be measured, and the blood vessel Ev to be measured is accurately illuminated with the measurement light. In this case, the ophthalmic technician can check and position tracking light and measurement light with higher precision by observing the eye fundus image Ea' displayed on the display 50 at a high zooming ratio.

Figure 12:
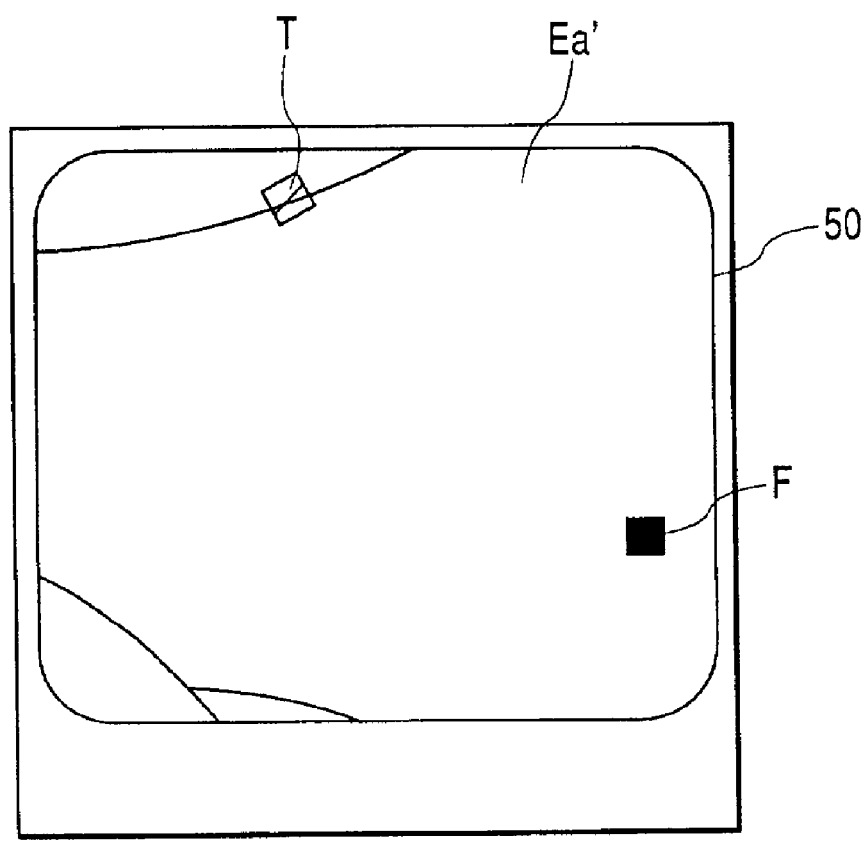
FIG. 12 is a view for explaining a display example of a zoomed and displayed observed eye fundus image.
Figure 14:
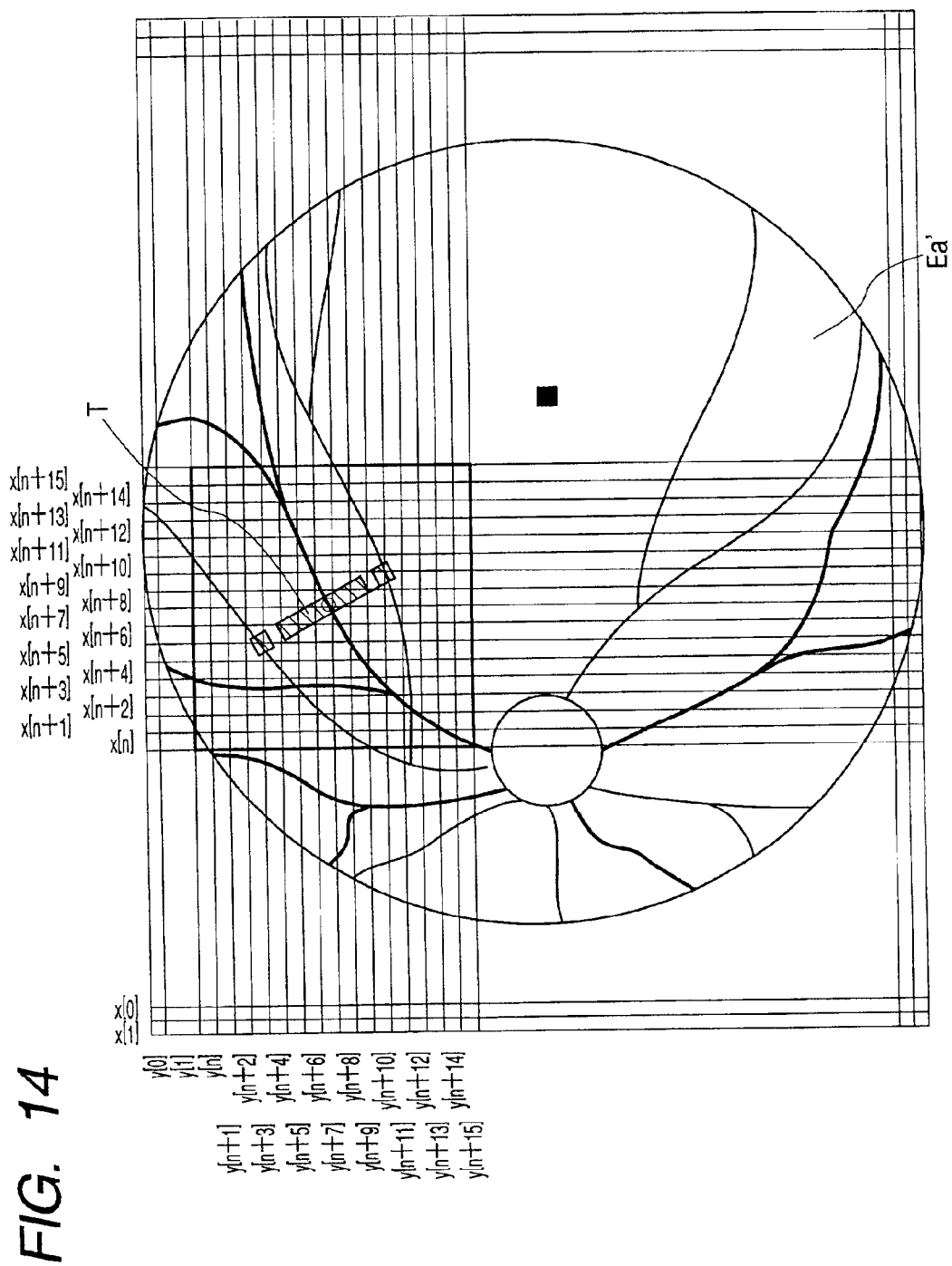
FIG. 14 is a view showing the pixel arrangement of the G signal in the two-dimensional CCD camera.

The ophthalmic technician therefore operates the input device 48 to zoom the eye fundus image Ea' displayed on the display 50. In this case, if the display zooming ratio is increased around the center of the eye fundus image Ea' picked up by the two-dimensional CCD camera 19, i.e., the central point of the coordinates of all pixels, the portions illuminated with the tracking target image T and measurement light may fall out of the display 50 so as not to be displayed, as shown in FIG. 12.

In this embodiment, therefore, the system controller 46 extracts the tracking target image T from the eye fundus image picked up by the two-dimensional CCD camera 19 and calculates its central position. The system controller 46 then performs control to zoom the eye fundus image Ea' around the calculated point and display the resultant image on the display 50.

RGB image data converted into digital data by the A/D converter 102 is input to the system controller 46 and stored in a frame memory (not shown).

If it is determined in step S100 that a zoom command is received from the input device 48, the G component of image data is read out from the frame memory in step S101. In this embodiment, the tracking light source 33 emits a green helium neon laser beam (wavelength: 543 nm). In addition, since an eye fundus image contains many R components, the system controller 46 uses the G signal of the R, G and B signals obtained by the two-dimensional CCD camera 19 to extract the tracking target image T and calculate a central position.

In step S102, the tracking target image T is extracted from the image data of the eye fundus image Ea'. FIG. 13 shows the result obtained by binarizing the gray scale levels of the G component image data of 16×16 pixels, i.e., pixels x[n] to x[n+15] and pixels y[n] to y[n+15] within the thick line frame in FIG. 14. The tracking target image T is formed on pixels each having a value of 1 in FIG. 13. Note that each of the pixels other than the tracking target image T has a value of 0.

In step S103, the position of the tracking target image T on the eye fundus image Ea' is calculated. The tracking target image T exists on the pixels x[n+6] to x[n+10] in the x direction and on the pixels y[n+4] to y[n+10] in the y direction. The middle point of these pixels in the x direction is given by {(n+10)−(n+6)}/2+(n+6)=n+8. The middle point in the y direction is given by {(n+10)−(n+4)}/2+(n+4)=n+7. That is, the central coordinates of the tracking target image T are (x[n+8], y[n+7]).

Figure 15:
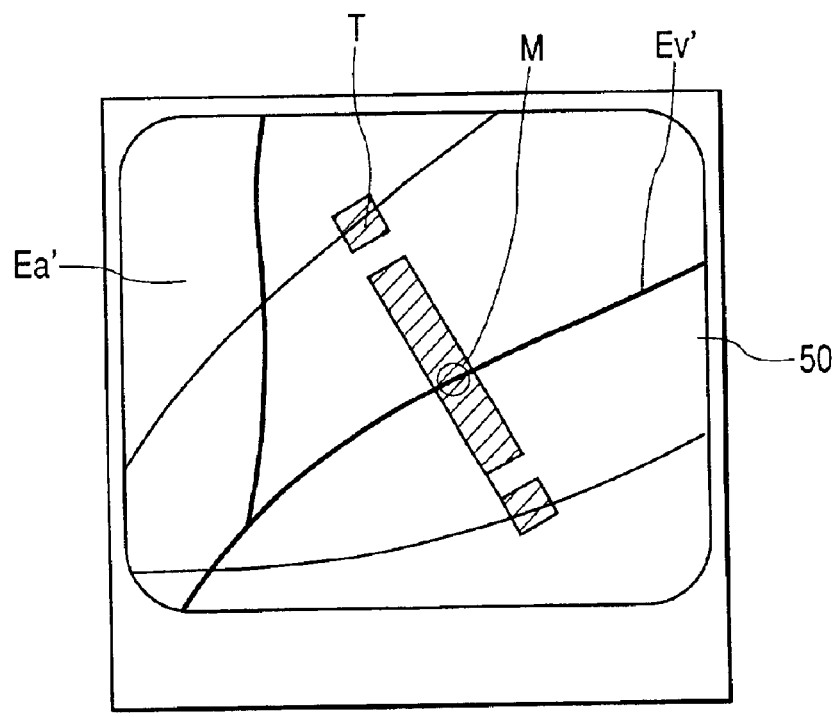
FIG. 15 is a view for explaining a display example of a zoomed and displayed observed eye fundus image.

In step S104, the system controller 46 centers the central coordinates of the tracking target image T calculated in step S102, and extracts pixel data to be displayed. In step S105, the system controller 46 outputs the pixel data to the D/A converter 103. As a consequence, a zoomed image is displayed on the display 50 with the central point of the tracking target image T being located in the center of the display 50, as shown in FIG. 15.

In this embodiment, when a zoom demand is input to the input device 48, the zooming ratio at which the eye fundus image Ea' displayed on the display 50 is zoomed is fixed to 3×. However, the zooming ratio may be variable, and the ophthalmic technician may set a zooming ratio through the input device 48.

In this embodiment, after the eye fundus Ea is illuminated with tracking light, the ophthalmic technician operates the input device 48 to zoom the eye fundus image Ea' displayed on the display 50. However, the eye fundus image Ea' displayed on the display 50 can be zoomed before the eye fundus Ea is illuminated with tracking light. In this case, since the position of the tracking target image T on the eye fundus Ea, which is calculated in step S103, cannot be calculated, the image data of the eye fundus image Ea' displayed on the display 50 is extracted around the central point of the coordinates of all pixels in step S104. Alternatively, the position of a measurement point may be determined on the basis of the position information of the image rotator 20 and galvanometric mirror 21, and an eye fundus image may be zoomed around the measurement point.

Figure 16:
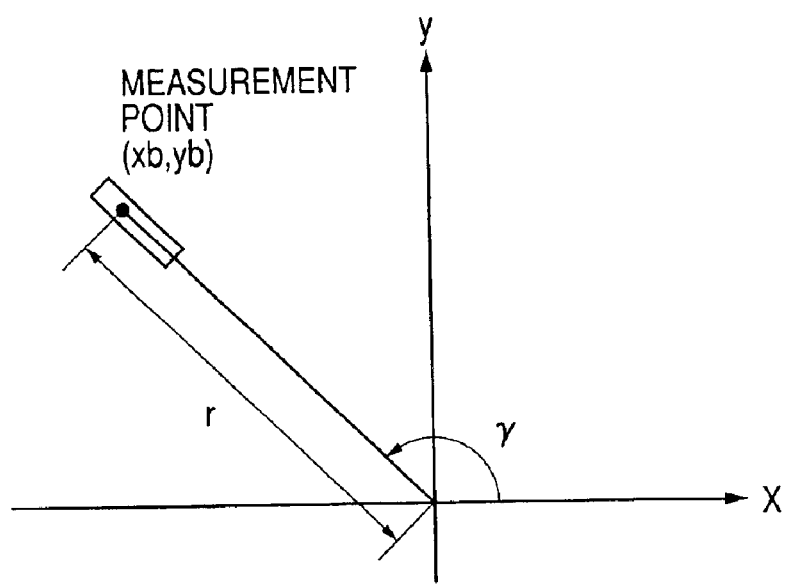
FIG. 16 is a graph for explaining the relationship between a measurement region and an optical axis.

FIG. 16 is a view for explaining the relationship between a measurement region and the optical axis of the objective lens 1. Letting n:n' be the zooming ratio of the galvanometric mirror 21 to a pupil Ep of the eye to be examined, δ be the offset angle of the galvanometric mirror 21, and δ' be the incident angle of tracking light and measurement light on the pupil Ep of the eye E to be examined with respect to the optical axis of the objective lens 2, then $$\tan \delta'/\tan 2\delta = n/n' \quad (1)$$

Letting (xb, yb) be the coordinates of a measurement point, r be the distance from the coordinates (0, 0) of the optical axis of the objective lens 1 on the eye fundus Ea to the coordinates (xb, yb) of the measurement point, and fe is the representative value of a model eye as the focal length of the eye E to be examined, equations (2) to (4) can be obtained from equation (1):

$$r = fe \cdot \tan \delta' = (n/n') \cdot fe \cdot \tan 2\delta \quad (2)$$

$$xb = r \cdot \cos \gamma = (n/n') \cdot fe \cdot \tan \delta \cdot \cos \gamma \quad (3)$$

$$yb = r \cdot \sin \gamma = (n/n') \cdot fe \cdot \tan \delta \cdot \sin \gamma \quad (4)$$

where γ is the angle defined by the measurement point (xb, yb) on the eye fundus Ea and the x-axis, i.e., the rotational angle of the image rotator 20. Note that the counterclockwise direction is set as a forward direction.

It is obvious from equations (3) and (4) that the position of a measurement point for the eye E to be examined with respect to the optical axis of the objective lens 1 is determined by the position information of the image rotator 20 and galvanometric mirror 21.

The system control part 46 calculates the position of a measurement point by the above method. In the flow chart of FIG. 11, this processing may be performed in place of steps S102 and S103.

With this processing, the eye fundus image Ea' illuminated with the tracking target image T and measurement light M is zoomed and displayed on the display part 50 such that the measurement point is located in the center, as shown in FIG. 15.

In the third embodiment, the ophthalmic technician changes the zooming ratio of the eye fundus image Ea' displayed on the display part 50 by operating the input device 48. However, the display zooming ratio of the display part 50 can also be changed automatically by detecting whether the eye fundus Ea is illuminated with tracking light.

Figure 17:
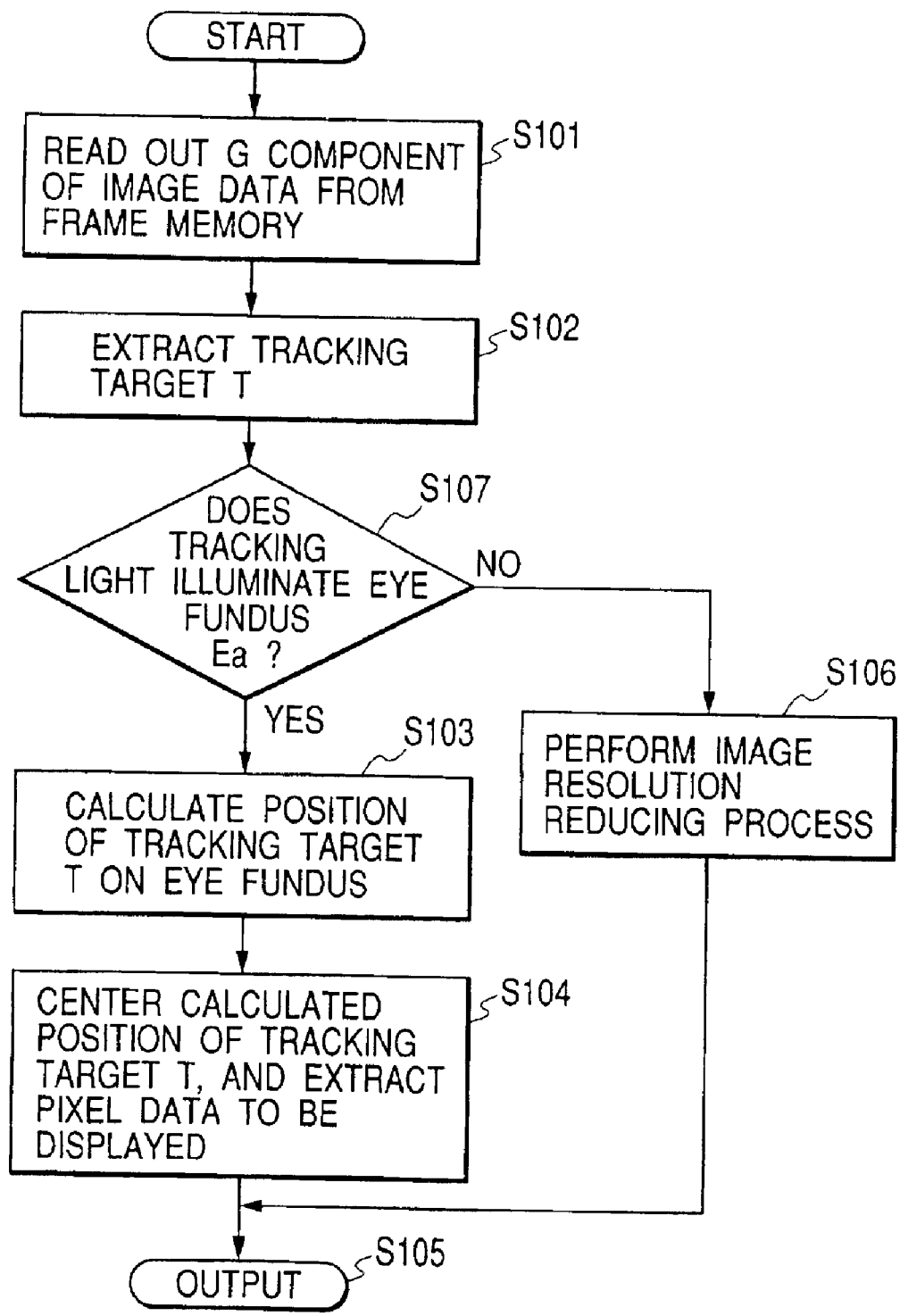
FIG. 17 is a flow chart in the fourth embodiment.

FIG. 17 is a flow chart in the fourth embodiment. The processing in steps S101 and S102 is the same as that in the third embodiment. In step S107, it is checked whether the eye fundus Ea is illuminated with tracking light. In step S102, the tracking target image T is extracted. In this case, if the tracking target image T is not detected, it is determined that the eye fundus Ea is not illuminated with tracking light. This determination may be done by checking whether information indicating that the eye fundus Ea is illuminated with tracking light is input to the input means 48.

If it is determined in step S107 that the eye fundus Ea is not illuminated with tracking light, image data is read out from the frame memory and processing for reducing the resolution is performed in step S106. In step S105, this data is converted into an analog video signal by the D/A converter 103. As a consequence, the tracking target image T and measurement light M are displayed on the display part 50, together with the observed eye fundus image Ea'. The ophthalmic technician can observe the eye fundus image Ea' shown in FIG. 10.

If it is determined in step S107 that the eye fundus image Ea' is illuminated with tracking light, the processing in steps S103 and S105 is performed in the same manner as in the third embodiment.

In this embodiment, it is checked whether the eye fundus Ea is illuminated with tracking light, and the display zooming ratio of the display part is automatically changed. In some case, however, it requires several sec to several 10 sec to allow accurate positioning of the tracking target image T, measurement light M, and blood vessel Ev to be examined after the ophthalmic technician operates the input means 48 to illuminate the eye fundus Ea with tracking light.

That is, in some case, it takes time for the ophthalmic technician to control the angle of the galvanometric mirror 21 by operating the rotator operation knob (not shown) before the tracking target image T is set to be almost vertical to the blood vessel Ev to be examined and a portion near the blood vessel Ev is illuminated with the measurement light M. Therefore, the display zooming ratio of the display part 50 may be automatically increased a predetermined period of time after the eye fundus Ea is illuminated with tracking light.

Alternatively, the display zooming ratio of the display part 50 may be automatically increased for the first time upon illumination of both tracking light and measurement light. After the illumination of tracking light is ended, the display zooming ratio may be automatically decreased.

As described above, the eye fundus examination apparatuses according to the third and fourth embodiments can change the display zooming ratio of an eye fundus image of an eye to be examined. Even if the display zooming ratio is further increased, since a position on the eye fundus of the eye to be examined at which tracking light and measurement light are applied is detected and control is performed to always set this position in almost the center of the display means, it never happen that tracking light and measurement light fall out of the display range of the display means and cannot be checked.

Since the ophthalmic technician can always observe, on a window on which an eye fundus image is zoomed, how a blood vessel to be measured is illuminated with tracking light and measurement light, he or she can check the illumination position of tracking light and measurement light and perform positioning more accurately. As a consequence, the precision of a measurement value can be further improved.

In addition, it is checked whether the eye fundus of an eye to be examined is illuminated with tracking light and measurement light, and the display zooming ratio and display position of an eye fundus image of the eye to be examined are changed on the basis of the detection result. This makes it possible to obtain the same effects as those described above without requiring any cumbersome manual settings.

In the third and fourth embodiments, the eye fundus blood flowmeters for measuring a blood flow on the eye fundus Ea have been described. However, these embodiments can also be applied to an ophthalmologic apparatus designed to simultaneously measure a blood vessel position and blood vessel diameter as well as a blood flow velocity. In addition, by combining the third and fourth embodiments with the first and second embodiments, an eye fundus image and data can be simultaneously displayed to be easily seen.

What is claimed is:

1. An eye fundus examination apparatus comprising
   (1) image pickup means for picking up an eye fundus image of an eye to be examined;
   (2) display means for displaying the eye fundus image picked up by said image pickup means;
   (3) display means for causing said display means to display a first image in which a measurement data and the eye fundus image are displayed together or a second image in which an enlarged eye fundus image is overlapped and displayed with a displayed measurement data;
   (4) laser beam illumination means for performing predetermined measurement with respect to a predetermined position of the eye fundus, and
   (5) control means for controlling the data display means and the laser beam illumination means,
   wherein said control means controls the data display means to change the first image to the second image when the laser beam illumination means irradiates a laser beam.

2. An apparatus according to claim 1, wherein said control means zooms an image displayed on said display means at the start of the laser beam illumination, and restores the image to the size before zooming at the end of the laser beam illumination.

3. An apparatus according to claim 1, further comprising:
   illumination means for illuminating an eye fundus of an eye to be examined;
   beam position detection means for detecting an illumination beam position; and
   display information control menus which can change at least one of a display position and a display enlarged ratio of the eye fundus image and a beam image displayed on said display means, in accordance with a detection result obtained by said beam position detection means.

4. An apparatus according to claim 3, wherein when the display position or display enlarged ratio is to be changed, the display position or display enlarged ratio is changed such that the beam position is displayed in a display area where the image is displayed.

5. An apparatus according to claim 3, wherein when the display position or display enlarged ratio is to be changed, the display position or display enlarged ratio is changed such that the beam position is displayed in a substantially center of a display area where the image is displayed.

6. An apparatus according to claim 5, wherein the display position or display enlarged ratio is changed a predetermined time after detection of the beam position.

7. An apparatus according to claim 3, wherein control is performed to display a low-zooming-ratio display image when the beam position cannot be detected, and to display a high-zooming-ratio display image when the beam position can be detected.

8. An apparatus according to claim 3, wherein both the eye fundus image and predetermined data can be displayed on said display means, and a method of displaying the eye fundus image and the predetermined data is changed when the beam position is detected.

9. An apparatus according to claim 3, further comprising instruction means for instructing to change at least one of a display position and display enlarged ratio of an image displayed on said display means.

10. An apparatus according to claim 1, wherein said control means changes the display state in accordance with the predetermined position.

11. An apparatus according to claim 3, further comprising
    (1) instruction signal input means for inputting an instruction signal for a measurement state to said control means,
    wherein the display state of said display means is changed in accordance with an instruction from said instruction signal input means.

12. An apparatus according to claim 11, wherein said control means changes the display state in accordance with the predetermined position.

13. An apparatus according to claim 1, wherein said eye fundus examination apparatus is an eye fundus blood flowmeter.

14. An apparatus according to claim 1, further comprising:
    (7) eye fundus illumination means for illuminating the eye fundus of the eye to be examined;
    (8) beam position detection means for detecting an illumination beam position; and
    (9) display information control means which can change at least one of a display position and a display enlarged ratio of the eye fundus image end a beam image displayed on said display means, in accordance with a detection result obtained by said beam position detection means.

15. An eye fundus examination apparatus according to claim 1, wherein the measurement data includes one of patient information, a measurement situation, and a measurement data.

* * * * *